United States Patent
Artsyukhovich (10) Patent No.: US 8,371,694 B2
(45) Date of Patent: Feb. 12, 2013

(54) BICHROMATIC WHITE OPHTHALMIC ILLUMINATOR

(75) Inventor: Alexander Artsyukhovich, San Juan Capistrano, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 241 days.

(21) Appl. No.: 12/948,294

(22) Filed: Nov. 17, 2010

(65) Prior Publication Data

US 2011/0149247 A1 Jun. 23, 2011

Related U.S. Application Data (60) Provisional application No. 61/287,425, filed on Dec. 17, 2009, provisional application No. 61/287,480, filed on Dec. 17, 2009.

(51) Int. Cl.
| | |
|---|---|
| A61B 3/10 | (2006.01) |
| A61B 18/18 | (2006.01) |
| A61N 5/06 | (2006.01) |
| A61N 1/30 | (2006.01) |

(52) U.S. Cl. ............. 351/221; 351/205; 606/4; 607/88; 604/21

(58) Field of Classification Search .......... 351/221, 351/200, 205, 213; 606/2–19; 128/898; 362/572; 607/88–95; 600/156–183; 604/4, 604/21

See application file for complete search history.

(56) References Cited

U.S. PATENT DOCUMENTS

| | | |
|---|---|---|
| 3,026,449 A | 3/1962 | Rappaport |
| 4,222,375 A | 9/1980 | Martinez |
| 4,656,508 A | 4/1987 | Yokota |
| 4,870,952 A | 10/1989 | Martinez |
| 4,883,333 A | 11/1989 | Yanez |
| 4,884,133 A | 11/1989 | Kanno et al. |
| 5,086,378 A | 2/1992 | Prince |
| 5,301,090 A | 4/1994 | Hed |
| 5,420,768 A | 5/1995 | Kennedy |
| 5,465,170 A | 11/1995 | Arimoto |
| 5,526,190 A | 6/1996 | Hubble, III et al. |
| 5,591,160 A | 1/1997 | Reynard |

(Continued)

FOREIGN PATENT DOCUMENTS

| | | |
|---|---|---|
| EP | 1114608 B1 | 3/2003 |
| JP | 2006087764 A | 4/2006 |

(Continued)

OTHER PUBLICATIONS

Abstract Only: Yasujima, H., et al; JP2006087764A; Publication Date Apr. 6, 2006; Machine translation; espacenet.com.

(Continued)

*Primary Examiner* — Dawayne A Pinkney
(74) *Attorney, Agent, or Firm* — Keiko Ichiye (57) ABSTRACT

An ophthalmic endoilluminator having only a first monochromatic light source emitting a first light and a second monochromatic light source emitting a second light. The first and second lights defining a light color axis representable on a chromaticity graph. A collimation element configured to collimate at least one of the first and second lights. An optical mixing device configured to mix the first and second lights into a single light beam. A lens configured to focus the single light beam. An optical fiber configured to carry the single light beam. A controller coupled to at least one of the first and second monochromatic light sources. The controller configured to tune at least one of the first and second monochromatic light sources such that the single beam of light represents a specific color of light at a point along the light color axis on the chromaticity graph.

20 Claims, 3 Drawing Sheets

U.S. PATENT DOCUMENTS

| | | | |
|---|---|---|---|
| 5,598,042 | A | 1/1997 | Mix et al. |
| 5,634,711 | A | 6/1997 | Kennedy et al. |
| 5,657,116 | A | 8/1997 | Kohayakawa |
| 5,736,410 | A | 4/1998 | Zarling et al. |
| 5,830,139 | A | 11/1998 | Abreu |
| 5,859,693 | A | 1/1999 | Dunne et al. |
| 5,997,163 | A | 12/1999 | Brown |
| 6,000,813 | A | 12/1999 | Krietzman |
| 6,015,403 | A | 1/2000 | Jones |
| 6,036,683 | A | 3/2000 | Jean et al. |
| 6,102,696 | A | 8/2000 | Osterwalder et al. |
| 6,120,460 | A | 9/2000 | Abreu |
| 6,123,668 | A | 9/2000 | Abreu |
| D434,753 | S | 12/2000 | Druckenmiller et al. |
| 6,183,086 | B1 | 2/2001 | Neubert |
| 6,190,022 | B1 | 2/2001 | Tocci et al. |
| 6,211,626 | B1 | 4/2001 | Lys et al. |
| 6,213,943 | B1 | 4/2001 | Abreu |
| 6,217,188 | B1 | 4/2001 | Wainwright et al. |
| 6,226,126 | B1 | 5/2001 | Conemac |
| 6,268,613 | B1 | 7/2001 | Cantu et al. |
| 6,270,244 | B1 | 8/2001 | Naum |
| 6,272,269 | B1 | 8/2001 | Naum |
| 6,336,904 | B1 | 1/2002 | Nikolchev |
| 6,431,731 | B1 | 8/2002 | Krietzman |
| 6,436,035 | B1 | 8/2002 | Toth et al. |
| 6,459,844 | B1 | 10/2002 | Pan |
| 6,730,940 | B1 | 5/2004 | Steranka et al. |
| 6,786,628 | B2 | 9/2004 | Steen et al. |
| 6,893,258 | B1 | 5/2005 | Kert |
| 6,917,057 | B2 | 7/2005 | Stokes et al. |
| 6,960,872 | B2 | 11/2005 | Beeson et al. |
| 7,025,464 | B2 | 4/2006 | Beeson et al. |
| 7,063,436 | B2 | 6/2006 | Steen et al. |
| 7,229,202 | B2 | 6/2007 | Sander |
| 7,276,737 | B2 | 10/2007 | Camras et al. |
| 7,301,271 | B2 | 11/2007 | Erchak et al. |
| 7,325,957 | B2 | 2/2008 | Morejon et al. |
| 7,344,279 | B2 | 3/2008 | Mueller et al. |
| 7,349,163 | B2 | 3/2008 | Angelini et al. |
| 7,403,680 | B2 | 7/2008 | Simbal |
| 7,482,636 | B2 | 1/2009 | Murayama et al. |
| 7,494,228 | B2 | 2/2009 | Harbers et al. |
| 7,556,412 | B2 | 7/2009 | Guillermo |
| 7,561,329 | B2 | 7/2009 | Zahniser et al. |
| 7,682,027 | B2 | 3/2010 | Buczek et al. |
| 7,918,583 | B2 | 4/2011 | Chakmakjian et al. |
| 7,990,587 | B2 | 8/2011 | Watanabe |
| 2001/0052930 | A1 | 12/2001 | Adair et al. |
| 2002/0003928 | A1 | 1/2002 | Bischel et al. |
| 2002/0087149 | A1 | 7/2002 | McCary |
| 2002/0137984 | A1 | 9/2002 | Chhibber et al. |
| 2003/0112421 | A1 | 6/2003 | Smith |
| 2003/0132701 | A1 | 7/2003 | Sato et al. |
| 2003/0147254 | A1 | 8/2003 | Yoneda et al. |
| 2003/0169603 | A1 | 9/2003 | Luloh et al. |
| 2003/0223248 | A1 | 12/2003 | Cronin et al. |
| 2003/0223249 | A1 | 12/2003 | Lee et al. |
| 2004/0004846 | A1 | 1/2004 | Steen et al. |
| 2004/0090796 | A1 | 5/2004 | Steen et al. |
| 2004/0124429 | A1 | 7/2004 | Stokes et al. |
| 2004/0233655 | A1 | 11/2004 | Zimmerman et al. |
| 2005/0018309 | A1 | 1/2005 | McGuire, Jr. et al. |
| 2005/0024587 | A1 | 2/2005 | Somani |
| 2005/0047172 | A1 | 3/2005 | Sander |
| 2005/0063171 | A1 | 3/2005 | Leitel et al. |
| 2005/0099824 | A1 | 5/2005 | Dowling et al. |
| 2005/0110808 | A1 | 5/2005 | Goldschmidt et al. |
| 2005/0140270 | A1 | 6/2005 | Henson et al. |
| 2005/0190562 | A1 | 9/2005 | Keuper et al. |
| 2005/0243539 | A1 | 11/2005 | Evans et al. |
| 2005/0270775 | A1 | 12/2005 | Harbers et al. |
| 2006/0203468 | A1 | 9/2006 | Beeson et al. |
| 2006/0262272 | A1 | 11/2006 | Anderson et al. |
| 2007/0102033 | A1 | 5/2007 | Petrocy |
| 2007/0133211 | A1 | 6/2007 | Yoneda et al. |
| 2007/0213618 | A1 | 9/2007 | Li et al. |
| 2007/0219417 | A1 | 9/2007 | Roberts et al. |
| 2007/0273290 | A1 | 11/2007 | Ashdown et al. |
| 2007/0284597 | A1 | 12/2007 | Nawashiro et al. |
| 2007/0291491 | A1 | 12/2007 | Li et al. |
| 2008/0030984 | A1 | 2/2008 | Harbers et al. |
| 2008/0073616 | A1 | 3/2008 | Dong et al. |
| 2008/0112153 | A1 | 5/2008 | Iwasaki et al. |
| 2008/0144169 | A1 | 6/2008 | Zahniser et al. |
| 2008/0175002 | A1 | 7/2008 | Papac et al. |
| 2008/0208006 | A1 | 8/2008 | Farr |
| 2008/0246919 | A1 | 10/2008 | Smith |
| 2008/0246920 | A1 | 10/2008 | Buczek et al. |
| 2008/0262316 | A1 | 10/2008 | Ajima et al. |
| 2008/0291682 | A1 | 11/2008 | Falicoff et al. |
| 2009/0036955 | A1 | 2/2009 | Han |
| 2009/0054957 | A1 | 2/2009 | Shanbaky |
| 2009/0095960 | A1 | 4/2009 | Murayama |
| 2009/0105698 | A1 | 4/2009 | Hodel et al. |
| 2009/0131823 | A1 | 5/2009 | Andreyko et al. |
| 2009/0154137 | A1 | 6/2009 | Bierhuizen et al. |
| 2009/0154192 | A1 | 6/2009 | Krattiger |
| 2009/0168395 | A1 | 7/2009 | Mrakovich et al. |
| 2009/0182313 | A1 | 7/2009 | Auld |
| 2009/0190371 | A1 | 7/2009 | Root et al. |
| 2009/0203966 | A1 | 8/2009 | Mizuyoshi |
| 2009/0219586 | A1 | 9/2009 | Fujimoto et al. |
| 2009/0227847 | A1 | 9/2009 | Tepper et al. |
| 2009/0092750 | A1 | 10/2009 | Herman |
| 2009/0267088 | A1 | 10/2009 | Peng et al. |
| 2010/0100006 | A1 | 4/2010 | Xu et al. |
| 2010/0127299 | A1 | 5/2010 | Smith et al. |
| 2010/0157620 | A1* | 6/2010 | Bhadri et al. ................. 362/554 |
| 2010/0182569 | A1 | 7/2010 | Artsyukhovich et al. |
| 2010/0228089 | A1 | 9/2010 | Hoffman et al. |
| 2010/0317923 | A1 | 12/2010 | Endo et al. |
| 2011/0009752 | A1 | 1/2011 | Chen et al. |
| 2011/0037948 | A1 | 2/2011 | Horvath et al. |
| 2011/0037949 | A1 | 2/2011 | Papac et al. |
| 2011/0038174 | A1 | 2/2011 | Papac et al. |
| 2011/0122366 | A1 | 5/2011 | Smith |
| 2011/0149246 | A1 | 6/2011 | Artsyukhovich |
| 2011/0149591 | A1 | 6/2011 | Smith |

FOREIGN PATENT DOCUMENTS

| | | |
|---|---|---|
| WO | 00/54655 A1 | 9/2000 |
| WO | 2008/133736 A2 | 11/2008 |

OTHER PUBLICATIONS

Abstract Only: Liu, C.K., et al.; "High Efficiency Silicon-Based High Power LED Package Integrated with Micro-Thermoelectric Device"; Microsystems Packaging, Assembly and Circuits Technology, pp. 29-33; 2007 Taipei Conference; IMPACT 2007; worldwide web: www.ieee.org; DOI 10.1109/IMPACT.2007.4433562.

PCT/US2012/052200 International Search Report dated Oct. 26, 2012.

* cited by examiner

BICHROMATIC WHITE OPHTHALMIC ILLUMINATOR

This application claims priority to U.S. Provisional Patent Application Ser. No. 61/287,425 filed on Dec. 17, 2009 and U.S. Provisional Patent Application Ser. No. 61/287,480 filed on Dec. 17, 2009.

BACKGROUND

There continues to be a need for improving ophthalmic illuminators used in ophthalmic surgery. Current ophthalmic illuminators utilize white light sources such as tungsten filament bulbs, halogen bulbs, and/or High Intensity Discharge (HID) lamps such as metal halide and Xenon lamps. However, there are many drawbacks to using the current ophthalmic illuminators.

For example, the bulbs and lamps used in current ophthalmic illuminators have a short life time. Because the bulbs and lamps burn out every 30-400 hours, they often burn out during a surgical procedure. Thus, such failures increase the risk of harm to the patient because of the immediate lack of light and the interruption of surgery. The bulb replacement cost is also very high in current ophthalmic endo illuminators.

Furthermore, these bulbs and lamps generate substantial amounts of heat such that current ophthalmic endo illuminators have to be made of components capable of withstanding high temperature. Because of the heat produced by the bulbs and lamps used in current ophthalmic illuminators a cooling fan is implemented within the illuminator which adds to the cost of production/use as well as increases the bulkiness/size of the illuminator. This fan also generates substantial levels of noise in the operating room. In use, these bulbs and lamps take a certain time period to warm up (e.g. tungsten filament to reach thermal equilibrium) during which the color and brightness produced by the ophthalmic illuminator changes.

No LED ophthalmic endo illuminators currently exist, but an RGB scheme has been proposed that mixes at least three monochromatic light sources such that illuminator produces a light having adjustable color, including white. Mixing three or more monochromatic light sources to produce a given light would require a complicated optical scheme in order for the three or more monochromatic light sources to be appropriately mixed. Additionally, the more monochromic light sources an ophthalmic illuminator is required to have to operate correctly the more opportunity there is for problems to occur if one of the light sources stops working. As compared to existing endo illuminators, any proposed LED endo illuminator should have a longer LED light source lifetime and "instant on" capability.

Accordingly, there remains a need for ophthalmic endo illuminators devices and methods for using during ocular surgery that use less than three monochromatic light sources, improve the quality of illumination (e.g. brightness and/or color), reduce the generation of heat and noise during use, increase reliability of the instrument during a surgical procedure, and extend the life span of the light source to eliminate any bulb replacement issues.

SUMMARY

These and other aspects, forms, objects, features, and benefits of the present invention will become apparent from the following detailed drawings and description.

An ophthalmic endoilluminator including a light source having only a first monochromatic light source emitting a first light and a second monochromatic light source emitting a second light. The first and second lights defining a light color axis representable on a chromaticity graph. Additionally, the ophthalmic endoilluminator includes a collimation element configured to collimate at least one of the first and second lights. In addition, the ophthalmic endoilluminator includes a mixing device configured to mix the first and second lights into a single light beam. Also, the ophthalmic endoilluminator has a lens configured to focus the single light beam. Furthermore, the ophthalmic endoilluminator has an optical fiber configured to carry the single light beam. Moreover, the ophthalmic endoilluminator has controller coupled to at least one of the first and second monochromatic light sources. The controller configured to tune at least one of the first and second monochromatic light sources such that the single beam of light represents a specific color of light at a point along the light color axis on the chromaticity graph.

An ophthalmic endoilluminator including a light source having only a first monochromatic light source emitting a first light having a first intensity and a second monochromatic light source emitting a second light having a second intensity. The first intensity being different than the second intensity. Additionally, the ophthalmic endoilluminator has a collimation element operable to collimate at least one of the first and second lights. In addition, the ophthalmic endoilluminator has a mixing device operable to mix the first and second lights into a single light beam. Also, the ophthalmic endoilluminator has a lens operable to focus the single light beam into a single fiber. Furthermore, the ophthalmic endoilluminator has an optical fiber operable to carry the single light beam. Moreover, the ophthalmic endoilluminator has a controller operable to alter the first and second intensities such that the single beam of light produces a specific color.

A method of providing illumination to an interior of an eye. The method including providing a light source having a first monochromatic light source and a second monochromatic light source. Additionally, the method includes providing current to the first and second monochromatic light sources to cause the first and second monochromatic light sources to emit a first and second light, respectively. In addition, the method includes collimating the first and second lights. Also, the method includes mixing the collimated light into a single light beam. Furthermore, the method includes focusing the single light beam. The method also includes transmitting the single light beam over an optical fiber. Moreover, the method includes controlling the first and second monochromatic light sources such that the single beam of light produces a specific color of light.

BRIEF DESCRIPTION OF THE DRAWINGS

In the accompanying drawings, which are incorporated in and constitute a part of the specification, embodiments of the invention are illustrated, which, together with a general description of the invention given above, and the detailed description given below, serve to exemplify the embodiments of this invention.

DETAILED DESCRIPTION

The present disclosure relates generally to the field of ophthalmic surgery, and more particularly to devices and methods for illumination in ophthalmic surgery. For the purposes of promoting an understanding of the principles of the invention, reference will now be made to embodiments or examples illustrated in the drawings, and specific language will be used to describe these examples. It will nevertheless be understood that no limitation of the scope of the invention is thereby intended. Any alteration and further modifications in the described embodiments, and any further applications of the principles of the invention as described herein are contemplated as would normally occur to one skilled in the art to which the disclosure relates.

Figure 1A:
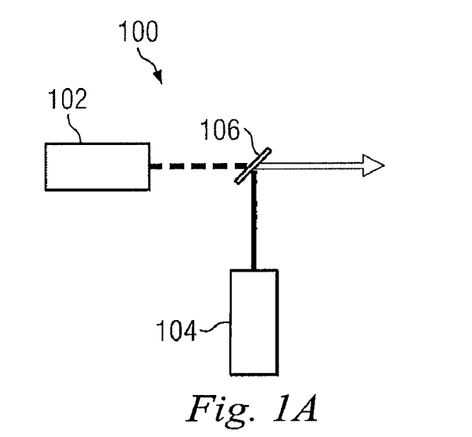
FIGS. 1A-B are diagrams of two monochromatic light sources forming bichromatic white illuminators that can be implemented in an ophthalmic endoilluminator according to an embodiment of the present disclosure.
Figure 1B:
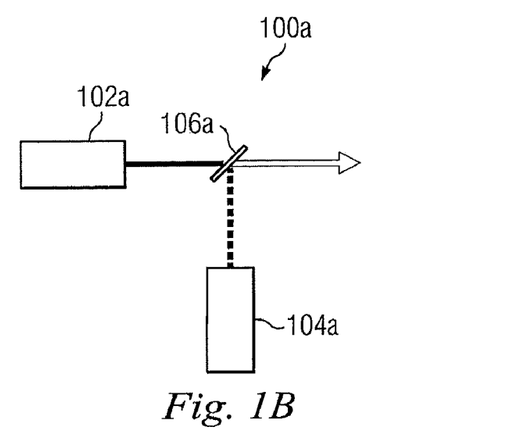

FIGS. 1A-B show diagrams of two monochromatic light sources forming bichromatic white illuminators that can be implemented in an ophthalmic endoilluminator according to an embodiment of the present disclosure. Referring first to FIG. 1A, a bichromatic white illuminator 100 that can be implemented in an ophthalmic endoilluminator is shown. Bichromatic white illuminator 100 has a first monochromatic light source 102, a second monochromatic light source 104, and a dichroic mirror 106. Monochromatic light source 102 is a first light emitting diode (LED) and monochromatic light source 104 is a second LED. More specifically, monochromatic light source 102 emits a light having a specific wavelength (i.e. color) while monochromatic light source 104 emits a light having a different specified wavelength (i.e. color) in the direction of dichroic mirror 106. In one specific example, monochromatic light source 102 emits a light having a turquoise color while monochromatic light source 104 emits a light having a red color. We define here "monochromatic light" as light with a narrow spectral band, centered on a certain central wavelength. The spectral width of this spectral band may be very narrow (<1 nm) for laser sources, and sufficiently wide (up to 100 nm or so) for LED sources.

Dichroic mirror 106 is transmissive to the light being emitted by monochromatic light source 102 (e.g. turquoise light) and is reflective to the light being emitted by monochromatic light source 104 (e.g. red light). In that regard, dichroic mirror 106 mixes the light being emitting from monochromatic light sources 102 and 104 into a single light beam. As will be described in greater detail below, because the light being emitted by the monochromatic light source 102 is of a specified wavelength (e.g. turquoise color) and the light being emitted by monochromatic light source 104 is of a specified different wavelength (e.g. red color) the mixing of these two lights enables bichromatic white illuminator 100 to produce a white light. In other words, bichromatic white illuminator 100 allows for the production of white light by mixing colors on opposite sides of a white region of a color spectrum (e.g. chromaticity graph) as will be described below in reference to FIG. 2.

FIG. 1B shows a bichromatic white illuminator 100a that can be implemented in an ophthalmic endoilluminator according to another embodiment. Bichromatic white illuminator 100a is similar to bichromatic white illuminator 100, but is comprised of different LEDs. In that regard, bichromatic white illuminator 100a has a first monochromatic light source 102a, a second monochromatic light source 104a, and a dichroic mirror 106a. Monochromatic light source 102a is a first LED emitting a light having a first wavelength (e.g. violet color) and monochromatic light source 104a is a second LED emitting a light having a second wavelength (e.g. yellow color).

Again, the monochromatic light sources 102a and 104a direct their light towards dichroic mirror 106a which is transmissive to the light being emitted by monochromatic light source 102a (e.g. violet color) and is reflective to the light being emitted by monochromatic light source 104a (e.g. yellow color). Dichroic mirror 106a mixes the lights being emitting from monochromatic light sources 102 and 104 into a single light beam. In other words, as will be described in greater detail below, dichromatic white illuminator 100a allows for the production of a white light by mixing colors on opposite sides of a white region of a color spectrum (e.g. chromaticity graph).

Although specific colors are discussed above for the monochromatic light sources of the respective bichromatic white illuminators 100 and 100a, it should be noted that other color combinations can be used as will be described below in reference to FIG. 2. Additionally, the specific arrangement of the monochromatic light sources and/or the properties of the dichroic mirrors in bichromatic white illuminators 100 and 100a are shown for exemplary purposes and not by way of limitation. In that regard, the monochromatic light sources in the exemplary embodiments can be repositioned with respect to any dichroic mirror such that one of the monochromatic light sources is reflective with respect to the dichroic mirror while the other monochromatic light source is transmissive with respect to the dichroic mirror. This mixing can be done by a number of other devices, for example dispersion prism.

Furthermore, it should be noted that the monochromatic light sources discussed above for bichromatic white illuminators 100 and 100a can be any energy sources that can produce light in the appropriate wavelengths. As a specific example, the light sources 100 and 100a can be lasers. Examples of the types of lasers that can emit the designated wavelengths include, by way of example but without limitation, Laser Diodes, Diode Pumped Solid State Lasers, Argon Lasers, and Helium Neon Lasers. In other words, dichromatic white illuminators 100 and 100a can utilize lasers each emitting the respective wavelength of a monochromatic light. As will be described in greater detail below with reference to FIG. 2, as long as the selected monochromic lasers emit specified wavelengths of light the two monochromatic lasers can be mixed to produce white light.

Figure 2:
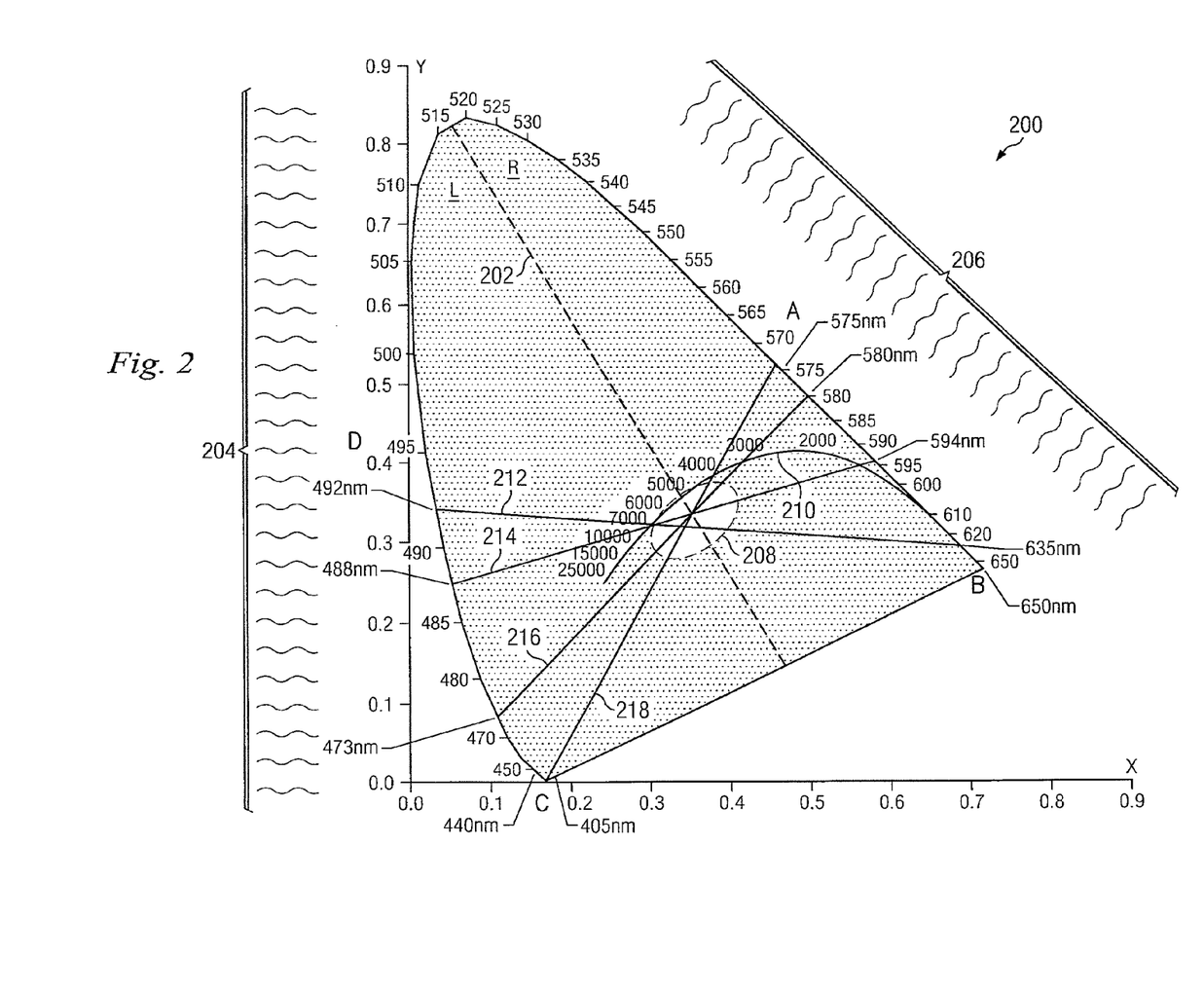
FIG. 2 is chromaticity diagram depicting a white light that can be produced by pairings of mono chromatic sources in a bichromatic white illuminator implemented in an ophthalmic endoilluminator according to an embodiment of the present disclosure.

FIG. 2 shows a chromaticity diagram 200, or graph, depicting a white light that can be produced by a bichromatic white illuminator implemented in an ophthalmic endoilluminator according to an embodiment of the present disclosure. For example, chromaticity diagram 200 can be considered a CIE 1931 chromaticity graph, a CIE 1976 chromaticity graph, or any other suitable chromaticity graph. Chromaticity diagram 200 generally represents the range of colors that are viewable by a human eye. More specifically, the diagram represents the range of colors that can be produced by a monochromatic light source such as sources 102, 102a, 104, and 104a discussed above.

As shown, the chromaticity diagram 200 is divided by a dividing line 202 such that the diagram is divided into a left half L and a right half R. In that regard, the right and left halves of the chromaticity diagram represent the possible colors capable of being produced by a monochromatic light source such as an LED or laser. Thus, the chromaticity diagram 200 is divided into two halves such that the left half L represents a first monochromatic light source 204 emitting a light having a wavelength less than approximately 518 nm and the right half R represent a second monochromatic light source 206 emitting a light having a wavelength greater than approximately 518 nm.

A white region 208 is shown adjacent a black body curve 210. As shown, dividing line 202 divides white region 208. White region 208 represents a region of white light capable of being produced by combining a monochromatic light source from each of the left and right halves of the chromaticity diagram 200. More specifically, white region 208 encompasses the different color temperatures of white light along or near black body curve 210 from the mixing and/or aligning the first and second monochromatic light sources 204 and 206. Therefore, dividing line 202 defines a reference point through white region 208 that allows for the production of white light by mixing the wavelength of light emitted from the first monochromatic light source 204 from the left half L with the wavelength of light emitted from the second monochromatic light source 206 from the right half R.

Monochromatic light sources 204 and 206 can be any monochromatic light source capable of emitting a light having a wavelength from about 400 nm to about 700 nm. In other words, monochromatic light sources 204 and 206 can be considered any light source capable of emitting a color falling within the spectrum of visible light. In that regard, FIG. 2 shows that monochromatic light source 204 emits a light having a wavelength of approximately less than 518 nm and monochromatic light source 206 emits a light having a wavelength of approximately more than 518 nm. For example, but not by way of limitation, monochromatic light sources 204 and 206 can be LEDs and/or lasers.

In that regard, when monochromatic light source 204 emits a light having a specified wavelength from the left half L and monochromatic light source 206 emits a light having a specified wavelength from the right half R, the resultant light produced by the mixture can be defined as a specific point along a light color axis that extends between the two sources. In other words, mixing the color of lights being emitted from monochromatic light sources 204 and 206 results in a light color axis on chromaticity diagram 200 that defines the range of possible colors capable of being produced by mixing the light emitted from monochromatic light sources 204 and 206. Furthermore, a combination of wavelengths of lights emitted from monochromatic light sources 204 and 206 can be selected such that the resultant light color axis extending between the two monochromatic light sources intersects white region 208 on chromaticity diagram 200. Thus, as will be described in greater detail below, given the appropriate combination of wavelengths that define a light color axis that intersect white region 208 results in the ability to tune the respective monochromatic light sources 204 and 206 such that the light being produced from mixing the two sources represents a point on the light color axis that is located within white region 208.

Although a combination of light emitted from the first monochromatic light source 204 from the left half L combined with a wavelength of light emitted from the second monochromatic light source 206 from the right half R can be used to produce white light, it has been found that an optimal effectiveness for producing white light is achieved when combining certain ranges of wavelengths. As shown in FIG. 2, a region CD of wavelengths (e.g. 495 nm-405 nm) and a region AB of wavelength (e.g. 575 nm-650 nm) represents the optimal regions of wavelengths to select for optimal effectiveness for producing white light using two monochromatic light sources. In other words, it is optimal when mixing monochromatic light sources 204 and 206 to produce white light to configure monochromic source 204 such that it emits a light having a wavelength falling within the region CD and to configure monochromatic light source 206 such that it emits a light having a wavelength falling within the region AB.

As shown in FIG. 2, for example, a light color axis 212 extends between monochromatic light sources 204 and 206. In that regard, light color axis 212 defines the possible range of colors capable of being produced from mixing an approximate 492 nm wavelength of light emitted from monochromatic light source 204 with an approximate 635 nm wavelength of light emitted from monochromatic light source 206. As shown, light color axis 212 intersects white region 208. Therefore, as will be described in greater detail below, monochromatic light sources 204 and 206 can be tuned such that the mixing of the approximate 492 nm wavelength of light emitted from monochromatic light source 204 with an approximate 635 nm wavelength of light from monochromatic light source 206 produces a light at a point along light color axis 212 that is located within white region 208.

Additionally, FIG. 2 shows light axes 214, 216, and 218 as examples of additional light axes that extend between monochromatic light sources 204 and 206 that intersect white region 208. For brevity purposes, the discussion above with respect to light color axis 212 is applicable to light axes 214, 216, and 218 except that the respective wavelengths of light being emitted from monochromatic light sources 204 and 206 have been changed. Table 1 below shows the various combinations of light wavelengths being produced by monochromatic light source 204 and 206 that define light axes 212, 214, 216, and 218 that intersect white region 208 of the color spectrum shown in chromaticity graph 200.

TABLE 1

Light Axes Intersecting White Region

| Light Color Axis | Monochromatic Light Source 204 | Monochromatic Light Source 206 |
|---|---|---|
| 212 | 492 nm (DPSS) | 635 nm (LD) |
| 214 | 488 nm (Ar) | 594 nm (HeNe) |
| 216 | 473 nm (DPSS) | 580 nm (DPSS) |
| 218 | 405 nm (LD) | 575 nm (DPSS) |

Although Table 1 above shows specific examples of combinations of wavelengths of light that produce light axes that intersect white region 208, the table is to be considered for exemplary purposes only and not to be construed as any explicit or implicit limitation of possible combinations of wavelengths that can be used. Further, for each wavelength, an example light source is included in the table. Moreover, the combination of wavelengths presented in Table 1 includes wavelengths selected from regions AB and CD and this in no way implies a limitation of the possible ranges of wavelength combinable from either side of dividing line 202 of chromaticity graph 200 that can be used to define a light color axis that intersects white region 208.

As discussed above, when mixing the light emitted by monochromatic light sources 204 and 206 a color of light is produced that corresponds to a point along a light color axis defined between the two monochromatic light sources. By tuning monochromatic light sources 204 and 206 a specific color corresponding to a point along the light color axis defined between the two monochromatic light sources can be achieved. The tuning of monochromatic light sources can be accomplished by altering the intensity (i.e. actual intensity or perceived intensity) of the respective monochromatic light sources.

In that regard, altering the actual intensity of monochromatic light sources 204 and 206 involves changing the relative intensity of the two monochromatic light sources relative to one another. By changing the intensity of monochromatic light source 204 relative to monochromatic light source 206, or vice versa, a specified color along a light color axis that extends between monochromatic light sources 204 and 206 can be produce. Generally, changing the relative intensity of monochromatic light sources 204 and 206 can be accomplished through various techniques such as, for example, pulse amplitude modulation and other suitable techniques. Using such techniques to drive monochromatic light sources 204 and 206 involves the two monochromatic light sources emitting light simultaneously, but being driven by separate currents having different intensity amplitudes. Thus, by tailoring, or selecting, the relative amplitude intensities between, for example, monochromatic light sources 204 and 206, one can create any color corresponding to a point along the light color axis that extends between the monochromatic light sources.

Because monochromatic light sources 204 and 206 are capable of emitting a wavelength of light on opposing sides of dividing line 202 of chromaticity graph 200 (see FIG. 2), a combination of wavelengths can be selected such that a light color axis defined between the monochromatic light sources 204 and 206 intersects white region 208. For example, one could use Table 1, shown above, to select a combination of wavelengths that define a light color axis between monochromatic light sources 204 and 206 that intersects white region 208. Therefore, a white light, or hue of white light, is produced by altering the respective intensities of monochromatic light sources 204 and 206 until the point along the light color axis at which the color being produced from mixing the light emitted from monochromatic light sources 204 and 206 corresponds to a point that is located within white region 208.

Figure 3:
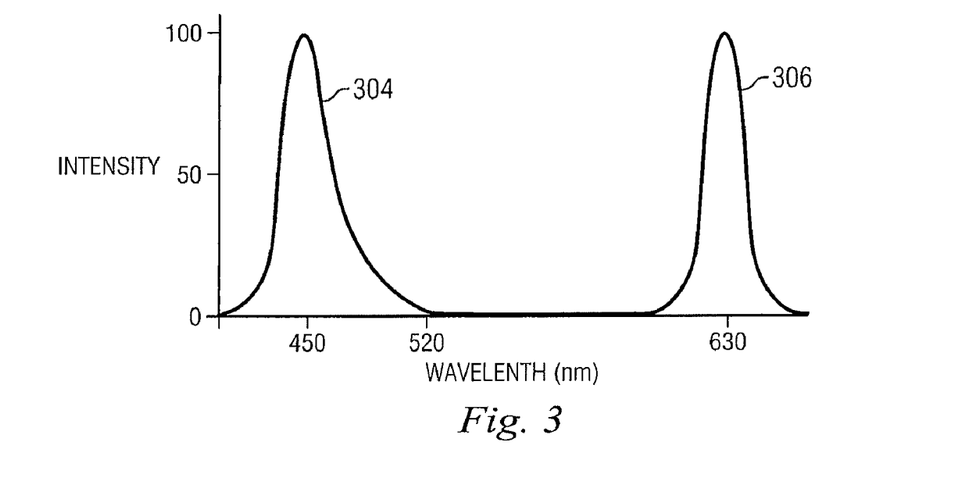
FIG. 3 is a graph of light intensity versus the wavelengths (spectra) emitted by two monochromatic light sources in a bichromatic white illuminator that can be implemented in an ophthalmic endoilluminator according to an embodiment of the present disclosure.

FIG. 3 shows a graph of light intensity versus the wavelengths emitted by two monochromatic light sources in a bichromatic white illuminator that can be implemented in an ophthalmic endoilluminator according to an embodiment of the present disclosure. As shown in FIG. 3, a monochromatic light source 304 emits a wavelength of light that is substantially blue in color and a monochromatic light source 306 emits a wavelength of light that is substantially red in color. For example, monochromatic light source 304 is a substantially blue LED or laser and monochromatic light source 306 is a substantially red LED or laser. Thus, monochromatic light sources 304 and 306 are capable of emitting a wavelength of light from the CD region and AB region of chromaticity graph 200 (see FIG. 2), respectively. Therefore, as an example, a white light, or hue of white light, is produced by altering the respective intensities of monochromatic light sources 304 and 306 until the point along the light color axis at which the color being produced from mixing the light emitted from monochromatic light sources 304 and 306 corresponds to a point that is located within white region 208.

It should be noted that the demonstration of monochromatic light sources 304 and 306 in FIG. 3 that are capable of emitting a light having a wavelength within a specified range is shown for exemplary purposes only. In that regard, any number of different combination of monochromatic light sources capable of emitting wavelength of light from about 400 nm to about 700 nm are contemplated herein as long as the monochromatic light sources are capable of emitting a wavelength of light on opposite sides of the dividing line 202 as shown in FIG. 2. Moreover, even though monochromatic light source 304 is generally identified as a blue LED or Laser and monochromatic light source 306 is generally identified as a red LED or laser, there are any number of other LEDs and/or lasers capable of emitting wavelengths of lights in the range of about 400 nm to about 700 nm. As such, it is contemplated that any number of other pairs of LEDs and/or lasers emitting a wavelength of light on opposite sides of dividing line 202 are contemplated for use herein.

Additionally, the tuning of monochromatic light sources 204 and 206 to produce a given color of light, such as white light, can be accomplished by changing the perceived intensity of these two monochromatic light sources. Changing the perceived intensity of monochromatic light sources 204 and 206 can be used to produce a specified color along a light color axis that extends between monochromatic light sources 204 and 206. As described in U.S. Pat. No. 7,286,146 titled "Method and System for LED Temporal Dithering to Achieve Multi-bit Color Resolution," which is hereby incorporated by reference in its entirety, the perceived intensity of monochromatic light sources 204 and 206 can be changed by sequentially alternating between the wavelengths of light being emitted by the monochromatic light sources at a sufficiently high rate (e.g., greater than 60 kHz) to create a visual perception of a desired color of light. Generally, this can be accomplished through various techniques such as, for example, pulse width modulation, temporal dithering, and other suitable techniques. Using such techniques to drive monochromatic light sources 204 and 206 involves supplying a substantially constant current to the respective monochromatic light sources 204 and 206 for particular periods of time. The shorter the period time that the substantially constant current is supplied to monochromatic light sources 204 and 206 the less brightness (i.e. perceived intensity) an observer will observe the light being emitted from monochromatic light sources 204 and 206. Thus, by cycling between, for example, monochromatic light sources 204 and 206, at different frequencies one can create any color corresponding to a point along the light color axis that extends between the monochromatic light sources.

Because monochromatic light sources 204 and 206 are capable of emitting a wavelength of light on opposing sides of dividing line 202 of chromaticity graph 200 (see FIG. 2), a combination of wavelengths can be selected such that a light color axis defined between the monochromatic light sources 204 and 206 intersects white region 208. For example, one could use Table 1, shown above, to select a combination of wavelengths that define a light color axis between monochromatic light sources 204 and 206 that intersects white region 208. Therefore, a white light, or hue of white light, is produced by cycling between monochromatic light sources 204 and 206, at a frequency corresponding to a point along the light color axis at which the color being produced from mixing the light emitted from monochromatic light sources 204 and 206 corresponds to a point that is located within white region 208.

It is contemplated that the tuning of monochromatic light sources 204 and 206 to produce a specific color, such as white light, via altering the respective intensities and perceived intensities of monochromatic light source are not mutually exclusive. Instead, it is contemplated that one can change the relative intensities of the light source in combination with the perceived intensities to produce a light that is located at a point along the light color axis that intersects white region 208.

Figure 4:
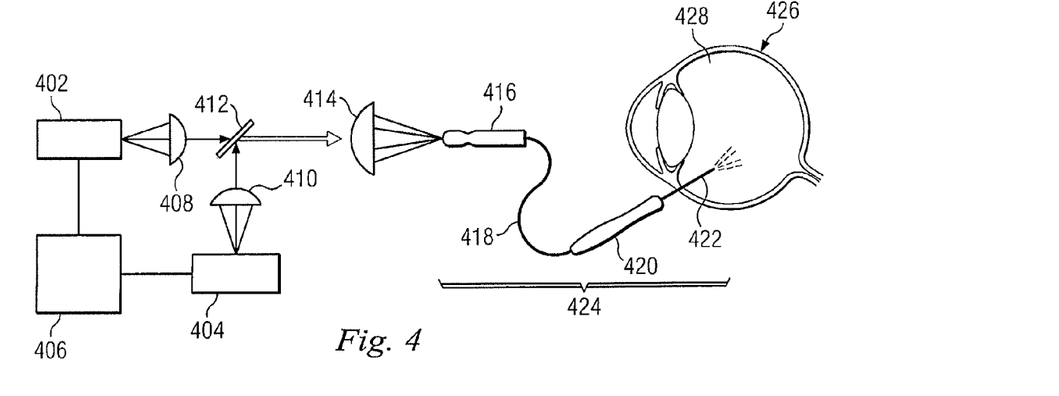
FIG. 4 is a diagram of an ophthalmic endoilluminator utilizing two monochromatic light sources according to an embodiment of the present disclosure.

FIG. 4 shows a diagram of an ophthalmic endoilluminator 400 utilizing two monochromatic light sources according to an embodiment of the present disclosure. More specifically, the ophthalmic endoilluminator 400 includes a first monochromatic light source 402, a second monochromatic light source 404, a controller 406, collimating lenses 408 and 410, a dichroic mirror 412, a condensing lens 414, a connector 416, an optical fiber 418, a hand piece 420, and a probe 422.

Controller 406 controls the operation of the various components of the ophthalmic endoilluminator 400. Controller 406 is typically an integrated circuit with power, input, and output pins capable of performing logic functions. Moreover, controller 406 can be configured to provide power to any component of ophthalmic endoilluminator 400. Additionally, in various embodiments controller 406 is a targeted device controller. In such a case, controller 406 performs specific control functions targeted to a specific device or component, such as directing current or current pulses to monochromatic light sources 402 and 404. In other embodiments, controller 406 is a microprocessor. In such a case, controller 406 is programmable so that it can function to control the current being supplied to monochromatic light sources 402 and 404 as well as other components of ophthalmic endoilluminator 400. Software loaded into the microprocessor implements the control functions provided by controller 406. In other embodiments, controller 406 can be any type of controller including a special purpose controller configured to control different components of ophthalmic endoilluminator 400. While depicted as one component in FIG. 4, controller 406 can be made of many different components or integrated circuits.

Controller 406 functions to control the operation of monochromatic light sources 402 and 404. In that regard, monochromatic light sources 402 and 404 are substantially similar to monochromatic light sources 204 and 206 discussed above with reference to FIG. 2. As discussed above, when mixing the light emitted by monochromatic light sources, such as 402 and 404, a color of light is produced that corresponds to a point along a light color axis defined between the two monochromatic light sources on a chromaticity graph (see FIG. 2). By tuning monochromatic light sources 204 and 206 a specific color corresponding to a point along the light color axis defined between the two monochromatic light sources can be achieved. The tuning of monochromatic light sources can be accomplished by altering the intensity or perceived intensity of the respective monochromatic light sources. Controller 406 can control the operation of monochromatic light sources 402 and 404, including altering the intensity and/or perceived intensity of the respective monochromatic light sources to produce a specific color of light, such as white light.

In that regard, controller 406 tunes monochromatic light sources 402 and 404 by various control schemes such as pulse width modulation, pulse amplitude modulation, temporal dithering, strobing, and/or other suitable control schemes that alter the intensity and/or perceived intensity of the respective monochromatic light sources. Moreover, controller 406 can drive monochromatic light sources 402 and 404 individually or together to produce different light outputs. Additionally, controller 406 can be programmed with a control scheme that calculates the appropriate combination of wavelengths of light that need to be emitted by monochromatic light sources 402 and 404, respectively, such that the combination of the wavelengths of light defines a light color axis that intersect white region 208. As discussed above with reference to FIG. 2, given the appropriate combination of monochromatic light sources results in the ability to tune the respective monochromatic light sources 402 and 404 such that the light being produced from mixing the two monochromatic light sources represents a point on the light color axis that is located within white region 208.

In one embodiment of the present invention, a surgeon interfaces with controller 406 to select the hue and/or temperature color of the light needed for a particular surgical procedure. For example, as discussed above, by tuning monochromatic light sources 204 and 206 a specific color corresponding to a point along the light color axis defined between the two monochromatic light sources can be achieved. However, in other embodiments, controller 406 can be programmed with several different light modes that provide several different colors of light output. These outputs may or may not be user selectable.

As discussed above, monochromatic light sources 402 and 404 are substantially similar to monochromatic light sources 204 and 206. Therefore, monochromatic light sources 402 and 404 can be any monochromatic light source capable of emitting a light having a wavelength from about 400 nm to about 700 nm. For example, but not by way of limitation, monochromatic light sources 204 and 206 can be LEDs and/or lasers. However, as discussed above with reference to FIG. 2, it is optimal if monochromatic light sources 402 and 404 emit light from opposing sides of dividing line 202. Moreover, when producing white light it is optimal that monochromatic light sources 402 and 404 emit wavelengths of light that define a light color axis that intersects white region 208 (see Table 1 and FIG. 2).

The light from monochromatic light sources 402 and 404 is collimated by collimating lenses 408 and 410, respectively. The collimation of light by collimating lenses 408 and 410 involves lining up the light rays from monochromatic light sources 402 and 404 such that the lights rays are parallel with a planar wave front. Moreover, the light from monochromatic light sources 402 and 404 is collimated so that the colors of light propagated by monochromatic light source 402 and 404 are independently collimated from each other. The respective collimated lights are combined into a single light beam by an alignment device such as dichroic mirror 412. In that regard, dichroic mirror 412 is transmissive to the collimated light emitted from monochromatic light source 402 and is reflective to the collimated light emitted from monochromatic light source 404. In other embodiments, dichroic beam splitters can be used in appropriate configurations to combine the collimated light into a single light beam.

As shown in FIG. 4, the single light beam from dichroic mirror 412 is focused by condensing lens 414. Condensing lens 414 focuses the single light beam so that it can be carried on a small gauge optical fiber. Condensing lens 414 is a lens of suitable configuration for ophthalmic endoilluminator 400. Condensing lens 414 is typically designed so that the resulting focused beam of light can be suitable transmitted by an optical fiber. Condensing lens 414 may be aspheric and serves to focus the single light beam.

Condensing lens 414 interfaces with an endoilluminator assembly 424. Endoilluminator assembly 424 includes connector 416, optical fiber 418, hand piece 420, and probe 422. Connector 416 is designed to connect optical fiber 418 to the focused beam of light exiting condensing lens 414. Specifically, connector 416 properly aligns the optical fiber 418 with the focused beam of light that is to be transmitted into eye 426. The beam of light exiting condensing lens 414 and entering connector 416 is a focused beam of different colors, each with their own intensity. Although not shown, the beam of light exiting condensing lens 414 and entering connector 416 may be carried by another optical fiber separate from optical fiber 418 in which connector 416 connects optical fiber 418 and the other optical fiber.

Optical fiber 418 extends through the entire length of endoilluminator assembly 424 to form a continuous path for light to travel into eye 426. Optical fiber 418 is typically a small gauge fiber that may or may not be tapered. Additionally, optical fiber 418 may be formed of one continuous strand or it may be formed of two or more optically coupled strands.

Optical fiber 418 also traverses through hand piece 420 and probe 422. In that regard, hand piece 420 is held by the surgeon and allows for the manipulation of probe 422 in eye 426. As shown in FIG. 4, probe 422 is inserted into eye 426 through an incision in the pars plana region. For example, probe 422 can be positioned to illuminate the inside or vitreous region 428 of eye 426 during vitreo-retinal surgery. When the focused beam carried by endoilluminator assembly 424 is backscattered against a surface of eye 426 to be illuminated, the resulting color hue is visible. In this manner, the respective colors of light emitted by monochromatic light sources 402 and 404 travel in a collimated and condensed beam through endoilluminator assembly 424 and into eye 426 where the light is backscattered from the fundus to produce, for example, an orange light. Thus, probe 422 provides an interface for illumination into eye 426.

Figure 5:
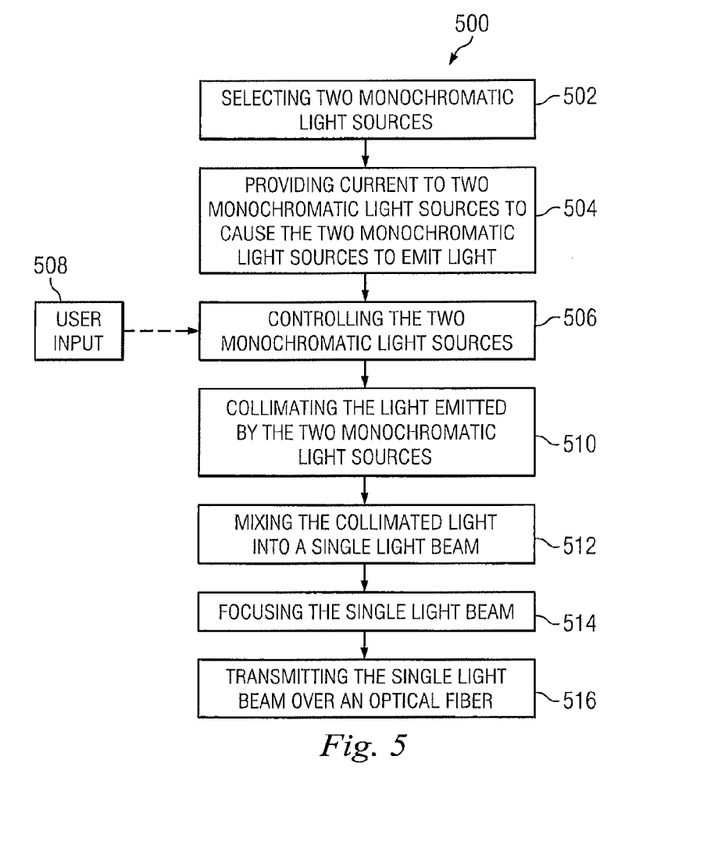
FIG. 5 is a method of operating an ophthalmic endoilluminator according to an embodiment of the present disclosure.

FIG. 5 shows a method 500 for operating an ophthalmic endoilluminator according to an embodiment of the present disclosure. In step 502, two monochromatic light sources are selected that emit specific wavelengths of light that when mixed together define a light color axis that intersects a white region of chromaticity graph. For example, as discussed above with reference to FIG. 2, Table 1 demonstrates various combinations of light wavelengths being emitted by monochromatic light sources 204 and 206 that define light axes 212, 214, 216, and 218 that intersect white region 208 of the color spectrum shown in chromaticity graph 200.

Next at step 504, current is provided to the two selected monochromatic light sources causing them to emit light. In step 506, the two monochromatic light sources are controlled such that the monochromatic light sources are tuned to produce a specified color of light when combined, such as a specific hue of white light. For example, as discussed above with reference to FIG. 2, monochromatic light sources can be tuned by changing the relative intensity or perceived intensity of the two monochromatic light sources. Therefore, a white light, or hue of white light, can be produced by tuning the monochromatic light sources such that the color of light being produced from mixing the light emitted from the monochromatic light sources corresponds to a point that is located within white region 208 of chromaticity graph 200 (see FIG. 2).

Step 506 can occur with or without user input. In other words, method 500 can be carried out automatically by an ophthalmic endoilluminator to produce a predefined color of light or allows for user input to produce a specified color of light. Optional step 508 represents user input that may be incorporated into the controlling of the two monochromatic light sources during step 506. It may be beneficial in some cases to lower the amount of potentially harmful blue light and shift white balance towards a yellow color along the blue-yellow color line. By lowering blue content in illumination the surgeon may illuminate the retina longer without achieving photic hazard level of exposure retina to intense illumination light. User input relates to the selection of the hue and/or temperature color of the light needed for a particular surgical procedure using the ophthalmic endoilluminator. User input can represent technical data/information, operational techniques, control schemes, and other suitable techniques relating to the tuning of the two monochromatic light sources to produce a specific color corresponding to a point along the light color axis defined between the two monochromatic light sources. Thus, optional step 508 allows for input into the selection of the hue and/or temperature color of the light needed for a particular surgical procedure using the ophthalmic endoilluminator.

After the monochromatic light sources are tuned to produce a specified color of light when combined, such as white light, the respective lights emitted from the monochromatic light sources are collimated during step 510. The lights emitted from the monochromatic light sources are independently collimated from each other. The collimated light can then be mixed into a single light beam at step 512. For example, during step 512 the respective collimated lights from the monochromatic light sources are combined into a single output beam by a dichroic mirror. In that regard, the dichroic mirror is transmissive to the collimated light emitted from one of the monochromatic light sources and is reflective to the collimated light emitted from the other of the monochromatic light sources.

Then the single light beam can be focused during step 514. In that regard, the single light beam from the dichroic mirror is focused by a condensing lens. The condensing lens focuses the single light beam so that the resulting focused beam of light can be suitably transmitted by an optical fiber.

Step 516 represents the transmission of the focused single light beam being transmitted over an optical fiber. For example, the optical fiber can be incorporated into an endoilluminator assembly, as shown in FIG. 4, such that during step 516 the transmission of the focused single light beam over the optical fiber includes transmission of the single light beam into an eye. When the focused single light beam carried by the optical fiber is backscattered against a surface of the eye to be illuminated, the resulting color hue is visible. Therefore, operating an ophthalmic endoilluminator according method 500, the respective colors of light emitted by the monochromatic light sources travel in a collimated and condensed focused single light beam through the optical fiber and into an eye where the light is backscattered to produce, for example, a white light.

The various monochromatic light sources disclosed herein can be considered solid state lighting, such as LEDs and/or lasers. Solid state lighting provides many advantages over current ophthalmic illuminators that use tungsten filament bulbs, halogen bulbs, and/or High Intensity Discharge (HID) lamps. For example, the LEDs and lasers generate less heat and consume less power than the bulbs and lamps used in conventional ophthalmic illuminators. The reduction in heat and power enables an ophthalmic illuminator to have a compact design because a cooling fan may no longer be needed and reduces operating costs by using less energy. Moreover, LEDs and laser have substantially longer life spans than the current the bulbs and lamps used in conventional ophthalmic illuminators. The longer life spans of LEDs and lasers as compared to the bulbs and lamps used in conventional ophthalmic illuminators reduces the likelihood of an interruption occurring during surgery and thereby deceases the risk of harm to a patient from the ophthalmic illuminator not operating at a certain point during a surgical procedure. Furthermore, the operating costs of using an ophthalmic illuminator using LEDs and/or laser as compared to current ophthalmic illuminator is lower because LEDs and lasers have a longer life span which requires less maintenance.

Additionally, for example, lasers have the ability to achieve a high degree of collimation and a low etendue. The low etendue of lasers allows for coupling with low etendue optical systems, for example, such as small core diameter optical fibers. In addition, LEDs and lasers have the ability to instantly be turned on and off without changes in brightness or color of illumination. Conventional bulbs and lamps, such as halogen bulbs, take a few seconds to reach thermal equilibrium during which time both the color and brightness change. Thus, solid state lighting provides many advantages over current ophthalmic illuminators that use tungsten filament bulbs, halogen bulbs, and/or High Intensity Discharge (HID) lamps.

Moreover, because currently proposed LED ophthalmic illuminators use three or more light sources the use of only two monochromatic light sources provides a much simpler solution. In that regard, mixing only two wavelengths of light to achieve a specified color, such as white light, allows for much simpler optical schemes as compared to mixing three or more light sources to achieve a specified color. Mixing of the two monochromatic light sources can be accomplished via a dichroic mirror that is designed to reflect and transmit the wavelength of lights from the respective monochromatic light sources. Additionally, in an alternative embodiment, when two lasers are used as the two monochromatic light sources the two lasers can be rotated into S and P polarization respectively to use a simple polarization cube for wavelength mixing to produce a specific color of light. Thus, using only two monochromatic light sources to produce a specified color of light provides a much simpler solution than as compared to using three light sources.

From the above, it may be appreciated that the present disclosure provides an improved system for illuminating the inside of the eye. The present invention provides a light source comprising two monochromatic light sources that can be driven in numerous different ways to provide a suitable light output. A probe containing an optical fiber carries the light into the eye. The present invention is illustrated herein by example, and various modifications may be made by a person of ordinary skill in the art.

While the present invention has been illustrated by the above description of embodiments, and while the embodiments have been described in some detail, it is not the intention of the applicant to restrict or in any way limit the scope of the invention to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general or inventive concept.

What is claimed is:

1. An ophthalmic endoilluminator comprising:
    a light source having only a first monochromatic light source emitting a first light and a second monochromatic light source emitting a second light, the first and second lights defining a light color axis representable on a chromaticity graph;
    a collimation element configured to collimate at least one of the first and second lights;
    a mixing device configured to mix the first and second lights into a single light beam;
    a lens configured to focus the single light beam;
    an optical fiber configured to carry the single light beam; and
    a controller coupled to at least one of the first and second monochromatic light sources, the controller configured to:
        determine from the chromaticity graph a combination of the first light and the second light that corresponds to a point along the light color axis on the chromaticity graph that represents a specific color; and
        tune at least one of the first and second monochromatic light sources according to the determined combination to yield the single beam of light at the specific color.

2. The ophthalmic endoilluminator of claim 1, wherein the light color axis intersects a white region of the chromaticity graph, the white region encompassing different color temperatures of white light along or near a black body curve.

3. The ophthalmic endoilluminator of claim 1, wherein the point is located within a white region of the chromaticity graph.

4. The ophthalmic endoilluminator of claim 1, wherein the chromaticity graph is a CIE 1931 chromaticity graph.

5. The ophthalmic endoilluminator of claim 1, wherein the first light is substantially turquoise in color and the second light is substantially red in color.

6. The ophthalmic endoilluminator of claim 1, wherein the first light is substantially violet in color and the second light is substantially yellow in color.

7. The ophthalmic endoilluminator of claim 1, wherein the first and second monochromatic light sources are selected from the group consisting of light emitting diodes and lasers.

8. An ophthalmic endoilluminator comprising:
    a light source having only a first monochromatic light source emitting a first light having a first intensity and a second monochromatic light source emitting a second light having a second intensity, the first intensity being different than the second intensity;
    a collimation element operable to collimate at least one of the first and second lights;
    a mixing device operable to align the first and second lights into a single light beam;
    a lens operable to focus the single light beam;
    an optical fiber operable to carry the single light beam; and
    a controller operable to:
        determine from a chromaticity graph a combination of the first light and the second light that corresponds to a point on the chromaticity graph that represents a specific color; and
        alter the first and second intensities according to the determined combination to yield the single beam of light at the specific color.

9. The ophthalmic endoilluminator of claim 8, wherein the controller is operable to alter the first and second intensities by changing a first amplitude intensity of the first light relative to a second amplitude of the second light to produce the specific color.

10. The ophthalmic endoilluminator of claim 8, wherein the controller is operable to alter the first and second intensities by sequentially alternating between the first light and the second light at a frequency to create the specific color.

11. The ophthalmic endoilluminator of claim 10, wherein the frequency is greater than 1 kHz.

12. The ophthalmic endoilluminator of claim 8, wherein the controller utilizes an algorithm to alter the first and second intensities, the algorithm selected from a group consisting of: an algorithm for strobing the first and second lights, a pulse width modulation algorithm, an amplitude modulation algorithm, and a temporal dithering algorithm.

13. The ophthalmic endoilluminator of claim 8, wherein the first light emitted from the first monochromatic light source has a wavelength greater than about 518 nm and the second light emitted from the second monochromatic light source has a wavelength less than about 518 nm.

14. The ophthalmic endoilluminator of claim 8, wherein the first and second monochromatic light sources are selected from the group consisting of light emitting diodes and lasers.

15. The ophthalmic endoilluminator of claim 8, wherein the first and second lights define a light color axis that intersect a white region on a chromaticity graph, the controller operable to alter the first and second intensities such that the single beam of light represents a point along the light color axis located within the white region.

16. A method of providing illumination to an interior of an eye, the method comprising:
 providing a light source having a first monochromatic light source and a second monochromatic light source;
 providing current to the first and second monochromatic light sources to cause the first and second monochromatic light sources to emit a first and second light, respectively;
 determining from a chromaticity graph a combination of the first and second lights that corresponds to a point on a light color axis of the chromaticity graph that represents a specific color;
 controlling the first and second monochromatic light sources such that a single beam of light produced from the first and second lights is the specific color;
 collimating the first and second lights;
 mixing the collimated light to yield the single light beam;
 focusing the single light beam; and
 transmitting the single light beam over an optical fiber.

17. The method of claim 16, wherein providing the light source includes selecting the first and second monochromatic light sources that define the light color axis that intersects a white region of the chromaticity graph.

18. The method of claim 16, wherein controlling the first and second monochromatic light sources includes altering an amplitude intensity of at least one of the first and second lights to yield the determined combination.

19. The method of claim 16, wherein controlling the first and second monochromatic light sources includes cycling between the first light and the second light at a frequency that yields the determined combination.

20. The method of claim 16, wherein controlling the first and second monochromatic light sources includes utilizing an algorithm to control at least one of the first and second monochromatic light sources, the algorithm selected from a group consisting of: an algorithm for strobing a light emitting diode, a pulse width modulation algorithm, and an amplitude modulation algorithm.

* * * * *